United States Patent [19]

Kojima et al.

[11] 4,110,376
[45] Aug. 29, 1978

[54] CYCLOPROPYLMETHYLAMINE DERIVATIVES

[75] Inventors: Atsuyuki Kojima, Nishinomiya; Junki Katsube, Toyonaka; Yoshito Kameno, Mino; Shigeho Inaba, Takarazuka; Hisao Yamamoto, Kobe, all of Japan

[73] Assignee: Sumitomo Chemical Company, Limited, Osaka, Japan

[21] Appl. No.: 605,012

[22] Filed: Aug. 15, 1975

[30] Foreign Application Priority Data

Aug. 15, 1974 [JP] Japan .................... 49-93881

[51] Int. Cl.² ............................................. C07C 87/32
[52] U.S. Cl. ........................... 260/570 R; 260/456 P; 260/459 A; 260/501.1; 260/558 R; 260/649 F; 260/649 R; 424/316; 424/330
[58] Field of Search ........... 260/501.1, 570.5, 570.1 R

[56] References Cited

U.S. PATENT DOCUMENTS

| 3,065,230 | 11/1962 | Baltzly et al. ............. | 260/570.5 X |
| 3,449,427 | 6/1969 | Kaiser et al. ............... | 260/570.8 |
| 3,462,491 | 8/1969 | Kaiser et al. ............... | 260/570 |
| 3,646,146 | 2/1972 | Teslino et al. .............. | 260/570.5 |
| 3,941,833 | 3/1976 | Gognaco .................... | 260/570.5 X |

OTHER PUBLICATIONS

Zirkle et al., "Journal Med. Chem.", vol. 5, pp. 1270-1272 (1962).

*Primary Examiner*—Robert V. Hines
*Attorney, Agent, or Firm*—Birch, Stewart, Kolasch and Birch

[57] ABSTRACT

Novel cyclopropylmethylamine compounds of the formula

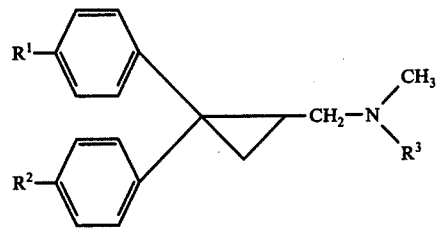

wherein $R^1$ and $R^2$ are each hydrogen or halogen and $R^3$ is hydrogen or methyl, and their non-toxic salts, which possess various useful pharmacological activities and can be produced by reduction of the corresponding compounds of the formula:

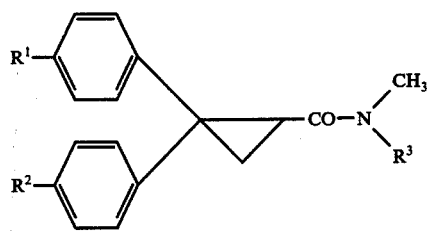

wherein $R^1$, $R^2$ and $R^3$ are each as defined above or their non-toxic salts, or by condensation of the corresponding compounds of the formula:

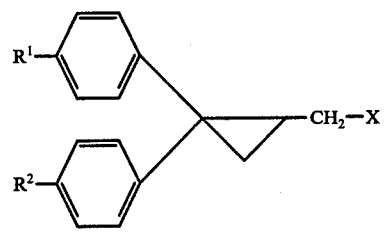

wherein $R^1$ and $R^2$ are each defined above, and X is a conventional interchangeable group such as halogen or sulfonyloxy with methylamine or dimethylamine.

5 Claims, No Drawings

CYCLOPROPYLMETHYLAMINE DERIVATIVES

The present invention relates to novel cyclopropylmethylamine derivatives, and their production and use.

The novel cyclopropylmethylamine derivatives provided by this invention are cyclopropylmethylamine compounds of the formula:

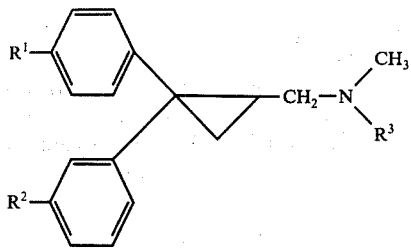

wherein $R^1$ and $R^2$ are each hydrogen or halogen and $R^3$ is hydrogen or methyl, and their non-toxic salts.

In the above significances, as "halogen", there may be exemplified chlorine, bromine, fluorine, etc.

Specific examples of the cyclopropylmethylamine compounds [I] are as follows:
N-Methyl-2,2-diphenylcyclopropylmethylamine;
N,N-Dimethyl-2,2-diphenylcyclopropylmethylamine;
N-Methyl-2,2-di(p-fluorophenyl)cyclopropylmethylamine;
N,N-Dimethyl-2,2-di(p-fluorophenyl)cyclopropylmethylamine;
N-Methyl-2,2-di(p-chlorophenyl)cyclopropylmethylamine;
N,N-Dimethyl-2,2-di(p-chlorophenyl)cyclopropylmethylamine;
N-Methyl-2,2-di(p-bromophenyl)cyclopropylmethylamine;
N,N-Dimethyl-2,2-di(p-bromophenyl)cyclopropylmethylamine;
N-Methyl-2-(p-fluorophenyl)-2-phenylcyclopropylmethylamine;
N,N-Dimethyl-2-(p-fluorophenyl)-2-phenylcyclopropylmethylamine;
N,N-Dimethyl-2-(p-chlorophenyl)-2-phenylcyclopropylmethylamine;
N,N-Dimethyl-2-(p-bromophenyl)-2-phenylcyclopropylmethylamine;
N,N-Dimethyl-2-(p-fluorophenyl)-2-(p-chlorophenyl)cyclopropylmethylamine;
N,N-Dimethyl-2-(p-fluorophenyl)-2-(p-bromophenyl)cyclopropylmethylamine;
N,N-Dimethyl-2-(p-chlorophenyl)-2-(p-bromophenyl)cyclopropylmethylamine, etc.

The cyclopropylmethylamine compounds [I] can form acid addition salts (e.g. hydrochloride, hydrobromide, sulfate, acetate, oxalate, citrate, tartrate, succinate, fumarate, lactate) and quaternary ammonium salts (e.g. methochloride, methiodide).

The cyclopropylmethylamine compounds [I] and their non-toxic salts exhibit various pharmacological properties and are useful as medicines. That is, these compounds antagonize the central nervous system depressant effects of tetrabenazine and reserpine, and moreover possess a mood elevating activity. Therefore, they may be useful as antidepressants and/or anorexics.

The cyclopropylmethylamine compounds [I] and their pharmaceutically acceptable salts can be administered parenterally or orally (with dosage adjusted to individual requirements) in the form of conventional pharmaceutical preparations. For instance, they can be administered in the form of conventional solid pharmaceutical preparations such as tablets or capsules, or in the form of conventional liquid pharmaceutical preparations such as suspensions, emulsions or solutions.

The cyclopropylmethylamine compounds [I] of the invention can be prepared from the corresponding compounds of the formula:

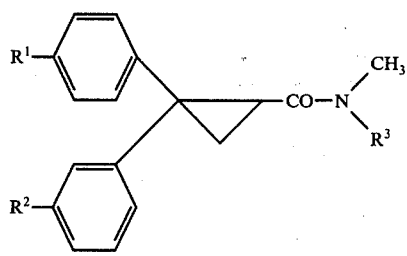

wherein $R^1$, $R^2$ and $R^3$ are each as defined above or their non-toxic salts by subjecting the latter to reduction. A reducing agent such as an alkali metal in an alcoholic solvent, a metal hydride or the like can be preferably employed. An electrolytic reduction can also be used for the purpose.

It is especially preferable to use a metal hydride such as lithium aluminum hydride, sodium aluminum diethyl dihydride or sodium bis(2-methoxyethoxy)aluminum hydride in an inert organic solvent such as diethyl ether, diisopropyl ether, tetrahydrofuran, dioxane, ethylene glycol dimethyl ether, heptane, hexane, cyclohexane, benzene or toluene. The temperature for the treatment in this case may be varied from ice-cooling to the refluxing temperature of the reduction system.

Sodium borohydride is another example of practically utilizable reducing agents, particularly when used in the presence of a salt such as aluminum chloride or on activation of the carboxamide group in the compound [II] with triethyloxonium fluoroborate or the like. Diborane is a further example of an efficient reducing agent.

The cyclopropylmethylamine compounds [I] can be also prepared by reacting the corresponding compounds of the formula:

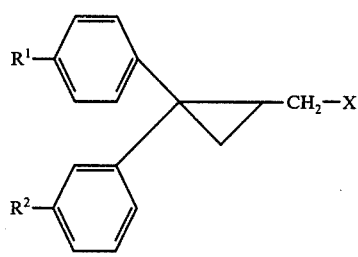

wherein $R^1$ and $R^2$ are each as defined above and X is a conventional interchangeable group such as halogen (e.g. chlorine, bromine) or sulfonyloxy (e.g. methanesulfonyloxy, p-toluenesulfonyloxy), with methylamine or dimethylamine in an inert organic solvent such as diethyl ether, diisopropyl ether, tetrahydrofuran, dioxane, ethylene glycol dimethyl ether, ethyl alcohol, methyl alcohol, benzene, toluene or pyridine in the presence or absence of an acid binding agent. Examples of the acid binding agent are pyridine, picoline, triethylamine, dimethylaniline, etc. The temperature for the treatment may be varied from ice-cooling to the refluxing temperature of the reaction system.

The cyclopropylmethylamine compounds [I] thus produced may be separated from the reaction mixture and purified by conventional procedures.

The obtained cyclopropylmethylamine compounds [I] may be converted into their salts by a conventional manner, and reconversion from the salts to the original free bases may be also carried out in a conventional manner.

The following examples are given for the purpose of illustration only, and it is not intended to limit the invention thereby.

EXAMPLE 1

To a solution of lithium aluminum hydride (0.30 g) in ether (10 ml) was added a solution of 2,2-diphenylcyclopropanecarboxylic acid N,N-dimethylamide (0.813 g) in ether (15 ml) under ice-cooling, and the resulting mixture was stirred under reflux for 2 hours. The reaction mixture was cooled, admixed with a 10% aqueous solution of sodium hydroxide (20 ml) and extracted with ether. The ether extract was dried over anhydrous magnesium sulfate and evaporated to afford N,N-dimethyl-2,2-diphenylcyclopropylmethylamine (0.701 g) as an oily substance. M.P. 231°–233° C (hydrochloride).

In the same matter as above, the following compounds were obtained:
N-Methyl-2,2-diphenylcyclopropylmethylamine, M.P. 240°–243° C (hydrochlorode);
N,N-Dimethyl-2,2-di(p-fluorophenyl)cyclopropylmethylamine, M.P. 186°–188° C (hydrochloride);
N-Methyl-2,2-di(p-fluorophenyl)cyclopropylmethylamine, M.P. 124°–126° C (hydrochloride).

EXAMPLE 2

To a solution of 40% aqueous dimethylamine (10 ml) in ethanol (10 ml) was added a solution of 2,2-diphenylcyclopropylmethyl chloride (0.50 g) in ethanol (10 ml) and triethylamine (1.0 g) at room temperature, and stirring was carried out at 35°–40° C for 32 hours. The reaction mixture was evaporated and poured into a 10% aqueous sodium hydroxide solution. The etheral extract was dried and chromatographed to afford N,N-dimethyl-2,2-diphenylcyclopropylmethylamine as an oily substance. M.P. 231°–233° C (hydrochloride).

In the same manner as above, the following compounds were obtained:
N-Methyl-2,2-diphenylcyclopropylmethylamine, M.P. 240°–243° C (hydrochloride);
N,N-Dimethyl-2,2-di(p-fluorophenyl)cyclopropylmethylamine, M.P. 186°–188° C (hydrochloride);
N-Methyl-2,2-di(p-fluorophenyl)cyclopropylmethylamine, M.P. 124°–126° C (hydrochloride).

What is claimed is:

1. A compound of the formula:

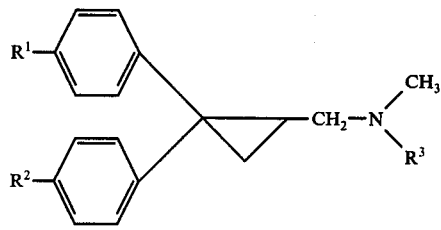

wherein $R^1$ and $R^2$ are hydrogen or halogen and $R^3$ is hydrogen or methyl, or a non-toxic salt thereof.

2. N,N-Dimethyl-2,2-diphenylcyclopropylmethylamine, or a non-toxic salt thereof.

3. N-Methyl-2,2-diphenylcyclopropylmethylamine, or a non-toxic salt thereof.

4. N,N-Dimethyl-2,2-di(p-fluorophenyl)cyclopropylmethylamine, or a non-toxic salt thereof.

5. N-Methyl-2,2-di(p-fluorophenyl)cyclopropylmethylamine, or a non-toxic salt thereof.

* * * * *